United States Patent
Ferrandis et al.

(10) Patent No.: US 7,385,024 B2
(45) Date of Patent: Jun. 10, 2008

(54) HETEROCARPINE, A HUMAN GHRH-BINDING PROTEIN

(75) Inventors: Eric Ferrandis, Saint Remy les Chevreuse (FR); Beng Poon Teng, Gif-sur-Yvette (FR); Christine Sohier, Saint Roch (FR); Christophe Thurieau, Paris (FR)

(73) Assignee: Societe de Counseils de Recherches et d'Applications Scientifiques (S.C.R.A.S.), Paris (FR)

( * ) Notice: Subject to any disclaimer, the term of this patent is extended or adjusted under 35 U.S.C. 154(b) by 480 days.

(21) Appl. No.: 10/470,112

(22) PCT Filed: Feb. 26, 2002

(86) PCT No.: PCT/FR02/00691

§ 371 (c)(1), (2), (4) Date: Jul. 24, 2003

(87) PCT Pub. No.: WO02/068461

PCT Pub. Date: Sep. 6, 2002

(65) Prior Publication Data

US 2004/0063621 A1    Apr. 1, 2004

(30) Foreign Application Priority Data

Feb. 27, 2001   (FR) ................... 01 02631

(51) Int. Cl.
*A61K 38/00* (2006.01)
(52) U.S. Cl. .............. 530/300; 514/2; 514/8; 514/12; 424/1.69; 435/69.1
(58) Field of Classification Search ........... 435/6; 530/300; 424/1.69; 514/2
See application file for complete search history.

(56) References Cited

FOREIGN PATENT DOCUMENTS

| WO | 9516707 | 5/1995 |
| WO | 0674007 | 9/1995 |

OTHER PUBLICATIONS

Gura. Cancer Models: Systems for identifying new drugs are often faulty. Science. 278: 1041-2, 1997.*
Manning et al. Stability of protein pharmaceuticals. Review. Pharm. Res., 6(11): 903-917, 1989.*
Suau et al, "(±)-Heterocarpine, . . . Heterocarpa", Phytochemistry (Oxford), vol. 49, No. 8, Dec. 1998, pp. 2551-2555.
Jaffe et al, "Suppression . . . Antagonist", Journal of Clinical Endocrinology and Metabolism, 1997, pp. 634-637.
H. Kiaris, A.V. Schally, J.L. Varga, K. Groot and P. Armatis Growth hormone-releasing hormone: An autocrine growth factor for small cell lung carcinoma 14894-14898 PNAS Dec. 21, 2999 vol. 96 No. 26.
Andreas Jungwirth, A. V. Schally, J. Pinski, K. Groot, P. Armatis Growth hormone-releasing hormone antagonist MZ-4-71 inhibits in vivo proliferation of Caki-I renal adenocarcinoma The National Academy of Sciences in the USA 0027-8424/97/945810-4 Apr. 7, 1997.
Jacek Pinski, A. V. Schally, K. Groot, G. Halmos, K. Szepeshazi, M. Zarandi, P. Armatis Inhibition of Growth of Human Osteocarsomas by Antagonists of Growth Hormone-Releasing Hormone Journal of the National Cancer Institute, vol. 87, No. 23 Dec. 6, 1995.
K. Szepeshazi, A.V. Schally, K. Groot, P. Armatis, F. Hebert G. Halmos Antagonists of growth hormone-releasing hormone (GH-RH) inhibit in vivo proliferation of experimental pancreatic cancers and decrease IGF-II levels in tumors European Journal of cancer 36 (2000) 128-136.
Najib Lamharzi, A. V. Schally, M. Koppan and K. Groot Growth hormone-releasing hormone antagonist MZ-5-156 inhibits growth of DU-145 human androgen independent prostate carcinoma in nude mice and suppresses the levels and mRNA expression of insulin-like growth factor II in tumors The National Academy of Sciences Medical Sciences vol. 95, pp. 8864-8868, Jul. 1998.

* cited by examiner

*Primary Examiner*—Cecilia Tsang
*Assistant Examiner*—Maury Audet
(74) *Attorney, Agent, or Firm*—Charles A. Muserlian

(57) ABSTRACT

The invention relates to a human GHRH-binding protein (human Growth Hormone-releasing hormone). Said protein, which is obtained from the *Pilocarpus Heterophyllus* plant, can be used to prepare medicaments intended to antagonise the effects of GHRH and to treat proliferative diseases (particularly cancer), acromegaly or diabetic nephropathies and retinopathies.

4 Claims, 4 Drawing Sheets

HETEROCARPINE, A HUMAN GHRH-BINDING PROTEIN

This application is a 371 of PCT/FR02/00691 filed Feb. 26, 2002.

The present invention relates to a human GHRH-binding (human Growth Hormone releasing hormone) protein.

Growth hormone ("GH") is a protein with 191 amino acids which stimulates the production of a number of growth factors, such as Insulin-Like Growth Factor I (IGF-1) and triggers the growth of a large number of tissues (skeleton, connective tissues, muscles and viscera). GH also has physiological activities, increasing the synthesis of the nucleic acids, proteins and lipolysis whilst reducing urinary secretions (Frohman L. A. & Kineman, R. D., *Handbook of Physiology*, Hormonal Control of Growth, edited by Kostyo, J. L. & Goodman, H. M. (Oxford Univ. Press, New York., 1999), p. 189-221).

The synthesis of GH is regulated by factors with positive or negative action secreted by the hypothalamus. The main factor controlling the production of GH is the "Growth Hormone Releasing Hormone" (GHRH), a peptide with 44 amino acids in humans.

GH and GHRH are involved in a number of diseases. Of these, the following should be mentioned in particular: cancer (in particular prostate or lung cancer), acromegaly, diabetic retinopathies and nephropathies; for these pathologies, treatment with GHRH antagonists is indicated. Due to the number of diseases potentially concerned, the industry continues to research GHRH antagonists.

The Applicant has therefore just isolated a new protein of vegetable origin, which has the property of binding human GHRH.

A first subject of the invention is therefore an isolated protein which can be obtained by extraction from the plant *Pilocarpus heterophyllus*, which is characterized in that it has a molecular mass of approximately 90.9 kDa and comprises fragments of peptide sequences SEQ.ID.NO. 1, SEQ.ID.NO. 2 and SEQ.ID.NO. 3, said protein being able to be presented in a glycosylated or non-glycosylated form. In order to simplify the disclosure which follows, this protein is hereafter called "heterocarpine".

Said SEQ.ID.NO. 1, SEQ.ID.NO. 2 and SEQ.ID.NO. 3 sequences are as follows:

```
SEQ. ID. NO.1:      KLIGARYFDK

SEQ. ID. NO.2:      YGEDIIVGVIDSGV

SEQ. ID. NO.3:      PESESY
```

The nomenclature used above (as in the remainder of the present Application) in order to define the peptides is that specified by the "IUPAC-IUB Commission on Biochemical Nomenclature" in which, in accordance with the standard representation, the N-terminal amino acid (amino group) appears on the left and the C-terminal amino acid (carboxyl group) appears on the right. The term "natural amino acid" indicates one of the natural L-amino acids found in the natural proteins: Gly, Ala, Val, Leu, Ile, Ser, Thr, Lys, Arg, Asp, Asn, Glu, Gln, Cys, Met, Phe, Tyr, Pro, Trp and His.

A protein is called "isolated" if it is taken out of its original environment. In particular, a natural protein is isolated if it is separated from the biological material with which it coexists in the natural system.

The invention preferably relates to heterocarpine in its non-glycosylated form.

According to a preferred variant of the invention, the heterocarpine is obtained from an extract of cells of the plant *Pilocarpus Heterophyllus* cultured in vitro.

Moreover, a subject of the invention is also a monoclonal antibody, or an antigen binding fragment of the latter, which specifically binds heterocarpine.

Heterocarpine has the property of binding human GHRH. In vitro, heterocarpine binds human GHRH and thus inhibits the synthesis of cyclic AMP induced during the binding of human GHRH on its receptor. In vivo, in rats, the heterocarpinehuman GHRH complex is formed in the blood compartment and, in dose-dependent manner inhibits the GH synthesis induced by 10 μg of human GHRH in a mole to mole ratio. The heterocarpine has the property of binding the human GHRH.

These properties render the compounds of the invention suitable for a pharmaceutical use. Therefore, a subject of the invention is also, as a medicament, heterocarpine in glycosylated or non-glycosylated form. It also relates to pharmaceutical compositions containing, as active ingredient, heterocarpine in a glycosylated or non-glycosylated form, said composition also comprising one or more pharmaceutically acceptable excipients. A further subject is the use of heterocarpine in a glycosylated or nonglycosylated form for preparing medicaments intended to antagonize the effects of GHRH, to treat proliferative diseases (and in particular cancer), to treat acromegaly or to treat diabetic retinopathies and nephropathies. With regard to cancer, heterocarpine is particularly suitable for preparing a medicament intended to treat carcinoid and pancreatic tumours, hypothalamo-hypophyseal gangliocytomas, bronchial, intestinal and hepatic carcinomas, sympathoadrenergic tumours, pheochromocytomas, hypophyseal adenomas and thyroid carcinomas.

A subject of the invention is also, as a medicament, a monoclonal antibody, or an antigen binding fragment of the latter, which specifically binds heterocarpine. It also relates to a pharmaceutical composition comprising, as active ingredient, a monoclonal antibody, or an antigen binding fragment of the latter, which specifically binds heterocarpine, said composition also comprising one or more pharmaceutically acceptable excipients. It relates moreover to the use of a monoclonal antibody, or of an antigen binding fragment of the latter, which specifically binds heterocarpine, for preparing medicaments intended to antagonize the effects of GHRH, to treat proliferative diseases (and in particular cancer), to treat acromegaly or to treat diabetic retinopathies and nephropathies. As regards cancer, said monoclonal antibody or said antigen binding fragment of the latter is particularly suitable for preparing a medicament intended to treat carcinoid and pancreatic tumours, hypothalamo-hypophyseal gangliocytomas, bronchial, intestinal and hepatic carcinomas, sympathoadrenergic tumours, pheochromocytomas, hypophyseal adenomas and thyroid carcinomas.

The invention also relates to the use of heterocarpine as an excipient in a pharmaceutical composition intended for the controlled release of GHRH. It also relates to a pharmaceutical composition comprising GHRH, heterocarpine and one or more pharmaceutically acceptable excipients.

Finally, other subjects of the invention are the processes making it possible to extract and isolate heterocarpine from cells of the plant *Pilocarpus Heterophyllus*, said cells preferably originating from in vitro cultures. These processes essentially include a stage of extraction of the cells from the plant *Pilocarpus Heterophyllus* with water at a temperature of 0 to 50° C., and preferably 4 to 25° C., said extraction stage being followed by a filtration stage to separate the heterocarpine-rich filtrate from the *Pilocarpus Heterophyllus* cells and by one or more stages of separation of the heterocarpine from the other components extracted from the plant *Pilocarpus Heterophyllus*.

According to a first variant, these extraction and isolation processes essentially include the following successive stages:
  a) a stage of extraction of the cells from the plant *Pilocarpus Heterophyllus* with water at a temperature of 0 to 50° C., and preferably of 4 to 25° C., said extraction stage being followed by a filtration stage to separate the heterocarpine-rich filtrate from the *Pilocarpus Heterophyllus* cells;
  b) a stage of precipitation of the proteins extracted, for example by adding ammonium sulphate, followed by a stage of separation of the precipitate (by filtration or, preferably, by centrifugation);
  c) solubilizing the precipitates recovered in Stage b) in water; and
  d) a stage of gel-filtration chromatography in order to separate the heterocarpine from the other components of the solution.

According to another variant, these extraction and isolation processes essentially include the following successive stages:
  a) a stage of extraction of the cells from the plant *Pilocarpus Heterophyllus* with water at a temperature of 0 to 50° C., and preferably 4 to 25° C., said extraction stage being followed by a filtration stage to separate the heterocarpine-rich filtrate from the *Pilocarpus Heterophyllus* cells;
  b) a stage of delipidation of the solution obtained in a), acidified by the addition of a non-oxidizing acid (for example hydrochloric acid, sulphuric acid or phosphoric acid) at a pH preferably comprised between 2 and 4, using liquid-liquid extraction (preferably by using an organic solvent such as dichloromethane, heptane, hexane or cyclohexane);
  c) a stage of elimination of the tannins by bringing the delipidated solution obtained in c) into contact with polyvinylpyrrolidone (or also nylon 66) followed by filtration on large-pore resin (preferably a polystyrene-based resin such as the resin Diaion® HP20);
  d) adjusting the filtrate obtained after Stage c) to alkaline pH (preferably between pH 9 and 11) by the addition of a base such as ammonium hydroxide, sodium hydroxide or potassium hydroxide;
  e) one or more stages of filtration on anion-exchange resin, the eluent for this stage or these filtration stages preferably being a buffer solution having a pH between 9 and 11 and optionally containing concentration gradients of a salt (such as for example sodium chloride or ammonium sulphate), in order to separate the heterocarpine from the other components of the solution; and
  f) a desalination stage consisting of passing the solution obtained in Stage e) over a resin separating the constituents of a mixture on the basis of their molecular mass (such as the resin Sephadex® G25 or Superdexe® 200 HR) and the elution of this mixture over said resin with water.

The pharmaceutical compositions containing a compound of the invention can be in solid form such as, for example, powders, pills, granules, tablets, liposomes, gelatin capsules or suppositories. The pills, tablets or gelatin capsules can be coated with a substance capable of protecting the composition from the action of gastric acid or the enzymes in the subject's stomach for a sufficient period of time to allow this composition to pass undigested into the latter's small intestine. The compound can also be administered locally, for example to the actual site of a tumour. The compound can also be administered according to a sustained-release process (for example by using a sustained-release composition or a perfusion pump). Appropriate solid supports can be, for example, calcium phosphate, magnesium stearate, magnesium carbonate, talc, sugars, lactose, dextrin, starch, gelatin, cellulose, methyl cellulose, sodium carboxymethyl cellulose, polyvinylpyrrolidine and wax.

The pharmaceutical compositions containing a compound of the invention can also be presented in liquid form such as, for example, solutions, emulsions, suspensions or a sustained-release formulation. Appropriate liquid supports can be, for example, water, organic solvents such as glycerol or glycols such as polyethylene glycol, as well as their mixtures, in varying proportions, in water.

The administration of a medicament according to the invention can be carried out by topical, oral, parenteral route, by intramuscular injection etc.

The dose of a compound according to the present invention, to be provided for the treatment of the above-mentioned diseases or disorders, varies depending on the administration method, the age and body weight of the subject to be treated as well as the state of the latter, and will be finally decided by the attending doctor or vet. Such a quantity determined by the attending doctor or vet is here called "therapeutically effective quantity".

In accordance with the invention, the heterocarpine can be prepared by the process described hereafter.

Preparation of Heterocarpine

According to a preferred variant of the invention, in vitro cultures of calluses or of cell suspensions originating from different organs of the plant have been carried out. These tissues cultured on semi-solid or liquid medium are able to bio-synthesize compounds having biological properties.

By "callus" is meant in the present Application a macroscopic cluster of undifferentiated cells of plants in culture on a semi-solid nutritive medium. The term "undifferentiated cells" in the present Application designates cells which have an aptitude under certain conditions to multiply in the form of a callus or of a cell suspension without any morphogenesis phenomenon. Finally, by "cell suspension", is meant undifferentiated cells which can form microscopic clusters in culture in a liquid nutrition medium.

The choice of the nutritive medium, hormones, culture conditions forms an integral part of the invention as well as the extraction and analysis of the extracts from these in vitro cultures.

Cells from *Pilocarpus Heterophyllus* seeds can be cultured in suspension for example according to the procedure hereafter.

The organs are decontaminated according to the usual methods before being cultured. Plantule organs in vitro have also served as callogenesis starting material without requiring disinfection beforehand. The preferred basic nutritive medium is one of the media commonly used for in vitro culture: this is Gamborg's medium (described in Gamborg et al., Nutrient requirements of suspension cultures of Soybean root cells, *Exp. Cell Res.* (1968), 50(1), 151-158). The carbon source is saccharose but glucose can also be used at a concentration of 1 to 120 g/l, preferably approximately 30 g/l. The macro-elements content can also be reduced by a factor of 2. Auxin or an auxin and a cytokinin are added to the medium, with a preference for a combination of both hormones, generally 2,4-dichlorophenoxyacetic acid and kinetin, but α-xnaphthaleneacetic acid (NAA), β-indoleacetic acid (IAA), β-indolbutanoic acid (IBA) or picloram can also be combined with the kinetin or benzylaminopurine (BAP). The concentration can vary from 0.1 to 10 mg/l for the auxin (for example 1 mg/l can be chosen), and from 0.01 to 2 mg/l for the cytokinin (for example 0.06 mg/l can be chosen). The vitamins are those associated with the different basic media. The cultures are carried out in light or in darkness. The temperature can vary from 10° C. to 33° C. but is preferentially approximately 23° C. The pH of the medium is comprised between 4 and 6.5 and is preferentially adjusted to 5.8 before sterilization. Moreover, agar may or may not be added to the medium.

The primary calluses appear after a few days of culture and can be separated from the original implant, removed and subcultured after approximately 1 month then cultured on agar semi-solid medium (in tubes or Petri dishes), at intervals of 4 to 8 weeks, preferably 6 weeks, thus a callus can be kept for years by successive subcultures on new media. The callus can also be subcultured in a stirred liquid culture medium (Erlenmeyer flask or bioreactor) with subcultures at 2 to 6 weeks, preferably 3 weeks.

The strains obtained are distinguished by their genetic origin, culture conditions, appearance and absence of morphogenesis.

The lyophilized *Pilocarpus Heterophyllus* cells are extracted with water at a temperature of 0 to 50° C., and preferably 4 to 25° C. The extract thus obtained is lyophilized before being redissolved at a suitable concentration (for example approximately 30% of dried matter). The proteins precipitated by the addition of a concentrated solution of ammonium sulphate (for example at a concentration representing 70 to 90% of the saturation concentration) are dissolved in a minimum of water and the insoluble materials are recovered by centrifugation. The proteins are then separated by column chromatography (the eluent preferably being water) and the heterocarpine (identifiable by its molecular mass of approximately 90.9 kDa) can then be recovered.

Preparation of Antibodies Specifically Binding Heterocarpine

The present invention provides binding agents, such as the antibodies which specifically bind heterocarpine. Such an agent is referred to as "specifically binding" a protein if it reacts at a detectable level (for example by an ELISA test) with said protein: and does not detectably react with other proteins. "The binding" refers to a non-covalent association between 2 separate molecules such that a complex is formed. The binding ability can be evaluated, for example, by determination of the binding constant for the formation of the complex. The binding constant is the value obtained when the value of the complex concentration is divided by the product of the values of the non-complexed component concentration. 2 products are called "bound" when the binding constant reaches 103 1/mol. The binding constant can be determined using methods well known to a person skilled in the art.

Any agent which can satisfy the above criteria can be regarded as a binding agent.

In the present invention, a binding agent is preferably an antibody or a fragment of the latter. The antibody can be prepared by any technique available to a person skilled in the art (cf. Harlow and Lane, *Antibodies: A Laboratory Manual*, Cold Spring Harbor Laboratory, 1988). In general, the antibodies can be produced by cell culture techniques including the generation of monoclonal antibodies or via transfections of antibody genes into host cells from bacteria or mammals in order to produce recombinant antibodies.

Among other techniques, use of those described hereafter is preferred. An immunogen containing heterocarpine is injected into a group of mammals (for example mice, rats, rabbits, sheep or goats). In this stage, the heterocarpine can serve as immunogen without modification. Alternatively, a superior immune response can be induced if the heterocarpine is combined with a transport protein such as bovine serum albumin or limpet haemocyanin. The immunogen is injected into the host animal, preferably according to a predetermined schedule, and the animals are bled periodically. Polyclonal antibodies specific to heterocarpine can thus be purified from such antiserum, for example, by affinity chromatography using heterocarpine coupled with an appropriate solid support.

Pharmaceutical Compositions Intended for the Release of GHRH

These compositions can in particular be prepared from heterocarpine and GHRH according to one of the methods described in the journal by De Wolf and Brett, *Pharmacological Reviews* (2000), 52, 207-236 and the references cited therein.

Unless otherwise specified, all the technical and scientific terms used here have the same meaning as that usually understood by an ordinary specialist in the field to which this invention belongs. Similarly, all the publications, patent applications, all the patents and all other references mentioned here are incorporated by way of reference.

The following examples are presented in order to illustrate the above procedures and should in no event be considered as a limit to the scope of the invention.

OBTAINING THE HETEROCARPINE

Example 1

Culture of Cells in Vitro:

A *Pilocarpus Heterophyllus* seed is germinated and the stem resulting from this germination is removed. Said stem is cultured in a Gamborg medium (Gamborg et al., Nutrient requirements of suspension cultures of Soybean root cells, *Exp. Cell Res*. (1968), 50(1), 151-158) to which 30 g/l of saccharose, 1 mg/l of 2,4-dichlorophenoxyacetic acid and 0.06 mg/l of kinetin have been added. The culture is carried out in tubes at a temperature of 23° C. and in darkness. Subcultures are carried out every 6 weeks under usual conditions. The strains, which are granular in appearance, have a beige pigmentation.

A growth kinetic of the strains, based on the increase in mass of fresh and dried material from the biomass, was carried out over 8 weeks. The calluses from 2 tubes are combined and constitute a twice-weekly harvest, the first harvest taking place at time 0. Calluses and gelose are then harvested and lyophilized. It is observed that growth is exponential up to 6 weeks of culture before the appearance of a stationary growth phase.

Extraction of the Cell Cultures:

25 g of lyophilized *Pilocarpus Heterophyllus* cells are extracted twice by immersion in 375 ml of water at 4° C., and left overnight at 4° C., then in 250 ml of water at 4° C. for 4 hours and finally washed with 125 ml of water at 4° C. Each aqueous solution thus obtained is filtered under vacuum through a glass filter surmounted with celite in order to separate the cell debris from the aqueous solution. The aqueous solutions thus combined are then lyophilized in order to obtain 9.4 g of dried material. The lyophilized dry extract is then dissolved in 31 ml of water at 20° C. in order to obtain a solution containing 30% of dry extract. 17.4 g of ammonium sulphate is added in small portions with constant magnetic stirring in order to precipitate the protein fraction. The protein precipitate is then separated from the ammonium sulphate solution by centrifugation at 3000 rpm for 20 minutes. The ammonium sulphate solution is decanted and the precipitated proteins are dissolved in 22 ml of water, re-centrifuged and filtered in order to eliminate the insoluble particles.

The filtrate obtained is then subjected to gel-filtration chromatography. It is injected into a column (Buchi N° 19678,L=230 mm; internal diameter=26 mm) filled with Superdex:™ 200 (Amersham Pharmacia Biotech, reference no. 17-1043-01; particles with an average diameter of 13 µm) prepared according to the manufacturer's recommendations using ultra-pure water (Water's Milli-Q) as eluent at a flow rate of 5 ml per minute. 40 ml fractions are thus collected and the active protein is found in the third and fourth fraction. These fractions are lyophilized in order to obtain approximately 14.2 mg of active product.

The purity of the product obtained is demonstrated by the appearance of a single band on electrophoresis gel containing sodium dodecylsulphate (SDS PAGE). The product corresponding to this band is designated hereafter as heterocarpine.

Example 2

The cells cultured in vitro according to the same procedure as that described in Example 1 above are extracted according to the method described hereafter. 100 g of lyophilized *Pilocarpus Heterophyllus* cells are extracted using 2 litres of demineralized water at 20° C., the mixture being maintained under stirring overnight. The cells and the extract are filtered by suction on frit (porosity 3, diameter 20 cm) covered by a celite bed (previously washed with acid; 1 to 2 cm thick). The cells recovered are washed with 400 ml of demineralized water before being eliminated. The aqueous filtrate is then acidified to pH 3.0 by the addition of approximately 10 ml of 18% hydrochloric acid. The acidified solution is then delipidated by liquid-liquid extraction using 400 ml of dichloromethane. The dichloromethane phase is decanted then eliminated. The delipidated solution is subjected to rotary evaporation in order to eliminate the residual dichloromethane. Approximately 30 g of polyvinylpyrrolidone is then added to the delipidated solution (pH approximately 3.0) and the mixture is stirred for approximately 30 minutes in order to eliminate the tannins. The mixture is filtered through a bed by suction on frit (porosity 3, diameter 10 cm) covered by a mixed bed comprising 25 g of celite (previously washed with acid) and 25 g of polyvinylpyrrolidone. The filtrate is then passed through a bed of 400 ml of Diaion® HP-20 (Mitsubishi Chemical Company) pre-activated according to the manufacturer's instructions. The resulting filtrate is then rendered alkaline (pH 10) by the addition of approximately 60 ml of a 20% ammonium hydroxide solution. A slight precipitation appears after 30 minutes of rest. 1 g of celite (previously washed with acid) is added to the alkaline solution which is then filtered by suction through a membrane filter (0.22 µm). Approximately 2 litres of filtrate are then passed through a HiPrep® Q XL 16/10 column, mounted on an Aktao purificator and pre-balanced at pH 10.2 with a piperazine/HCl 0.1M buffer, with a flow rate of 0.5 ml per minute (the HiPrepe® column and the Akta® purificator are both products from the company Amersham Biosciences). The column is then washed successively with 6 column volumes of the starting buffer at pH 10.2, 5 column volumes of the same buffer containing a 0.2M concentration of NaCl; and 10 column volumes of the same buffer containing a 1M concentration of NaCl. The majority of the heterocarpine is recovered in the first 3 column volumes of buffer containing the 1M concentration of NaCl. The active fractions are desalinated by passing through a Sephadex® G25 column (volume of the bed: 260 ml) using demineralized water as eluent. The active fractions, found in the first column volume corresponding with the hold-up volume, are then lyophilized in order to obtain 170 mg of heterocarpine. The heterocarpine thus obtained is practically single band on SDS PAGE gel.

CHARACTERIZATION OF THE HETEROCARPINE

Analysis and Micro-sequencing:

The samples are loaded onto a 10% polyacrylamide gel. After migration, the gels are fixed and stained with Coomassie blue.

The gel tracks represented in FIG. 3 corresponding to tracks 1, 2, 3, 4 and 5 are respectively the molecular weight marker (Amersham), 0.5, 1 and 2 µg of the content of the final heterocarpine fraction as obtained in Example 1 and the molecular mass marker (Amersham). Determination of the molecular mass by means of a standard molecular mass marker graph using standard computing tools well known to a person skilled in the art (for example, Viber Lourmat's Bio-Profil Bio1D software) makes it possible to show that heterocarpine has a molecular mass of 90.9 kiloDaltons (±1.6 kiloDaltons).

For protein micro-sequencing analysis, the band of polyacrylamide containing the protein is cut out and digested in 300 µl of digestion buffer containing 50 mM Tris (pH 8.6), 0.03% of sodium dodecylsulphate at 35° C. for 18 hours in the presence of 0.4 µg of endolysine-C (Sigma). The peptides obtained are separated, by HPLC, on a DEAE-C18 in-line column 1 mm in diameter. The separation gradient is based on a mixture of acetonitrile (from 2 to 70%) and 0.1% trifluoroacetic acid (TFA). The sequencing is then carried out on a Procise sequencer (Applied Biosystem). In this way three peaks have been sequenced, making it possible to characterize heterocarpine in a unique manner. The corresponding sequences are identified in the present Application by SEQ.ID.NO. 1, SEQ.ID.NO. 2 and SEQ.ID.NO. 3.

Analysis of the glycoproteins is carried out by the detection of sugared structures of the glycoproteins separated by SDS-PAGE gel. This detection system is a modification of the "Periodic Acid-Schiff" methods and leads to the appearance of magenta bands showing evidence of the glycoproteins (Sigma). For the heterocarpine as obtained in Example 1, the result reproduced in FIG. 4 is obtained.

PHARMACOLOGICAL PROPERTIES OF HETEROCARPINE

Stable Transfections of the Human GHRH Receptor (hGHRH-R):

Human embryo kidney cells, HEK-293, (a cell line developed by Dr. Stuart Sealfon, Mount Sinai Medical School, New York, N.Y.) expressing the human GHRH receptor in stable manner were obtained from Dr. Kelly Mayo (Northwestern University, Chicago, Ill).

Cell Culture and Membrane Preparation:

The HEK-293 cells transfected in a stable manner with the human GHRH receptor described above are cultured in DMEM (Dulbecco's modified Eagle's medium, high glucose content; supplied by Life technologies) supplemented with 0.4 mg/ml of G418 (Life technologies) in the presence of 10% of foetal calf serum and 4 mM of L-glutamine (Life technologies). The cells are homogenized in buffer A containing 50 mM HEPES (pH 7.4), 5 mM of magnesium chloride ($MgCl_2$), 2 mM of ethyleneglycol-bis(2-aminoethyl)-N,N,N',N'-tetraa acid (EGTA) and 50 µg/ml of bacitracin then are subjected to sonication in the same buffer A. The cells thus homogenized are centrifuged at 4° C. at 39,000 g for 10 minutes, suspended in buffer A and re-centrifuged at 4° C. at 40,000 g for 10 minutes. The total membrane proteins are quantified by Bradford's technique. The pelleted membranes are thus stored at −80° C. for later use.

Competitive Binding Test on hGHRH-R:

The membranes of the HEK-293 cells transfected in a stable manner with the human GHRH receptor are diluted to a concentration of 100 µg/ml in the reaction buffer containing 50 mM HEPES (pH 7.4), 5 mM of $MgCl_2$, 2 mM of EGTA, 50 µg/ml of bacitracin and 0.5% of bovine serum albumin (BSA). The membranes are incubated with 0.05 nM of [$^{125}$I]GHRH(1-44 amide) (Amersham) in a final volume of 200 µl in the presence of increasing concentrations of heterocarpine for 2 hours at 23° C. The reaction is stopped by rapid filtration on 96-well GF/C filters 0.1% pre-loaded with polyethylenimine. The filters are then washed three times at 4° C. with washing buffer containing 50 mM Tris (pH 7.4) using a Packard 96-well filtration station. The filters thus dried are submerged in 20 µl of scintillating cocktail (Microscint O, Packard) and are subjecting to Topcount counting (Packard). The non-specific activity is determined in the presence of 100 nM of hGHRH. A dose-response curve is generated for hGHRH (0.001 nM-100 riM) and the results obtained are included in FIG. 1.

Competitive Formation of Cyclic AMP:

The HEK-293 cells transfected in a stable manner with the human GHRH receptor are distributed in 48-well culture plates and cultured for 3 days. The culture medium is then removed and replaced by medium B containing 250 µl of DMEM (Dulbecco's modified Eagle's medium, high glucose content; supplied by Life technologies) in the presence of 0.5% of BSA, 0.5 mM of 3-isobutyl-1-methylxanthine (IBMX) and pre-incubated for 5 minutes at 37° C. At the end of the pre-incubation period, the heterocarpine is tested for an additional 20 minutes. The concentrations observed are reported in FIG. 2. The incubation is stopped by the addition of 100 µl of O.1M HCl and the aliquots are analysed for their cyclic AMP content using the FlashPlate kit (New England Nuclear).

Assay of GH in Rats:

Levels of GH in rats (Sprague Dawley males) are measured in blood samples by an enzymo-immunological test developed by Spi-Bio (Spi-Bio, France). The rats are treated by intravenous injection of heterocarpine at increasing doses (vehicle alone, 1, 3 and 10 nmol), then, 10 minutes after, by intravenous injection of 10 µg (3 nmol) of hGHRH. Ten minutes after injection of the hGHRH, the growth hormone levels are measured in the blood samples as described above. The results obtained are represented in FIG. 5.

SEQUENCE LISTING

<160> NUMBER OF SEQ ID NOS: 3

Figure 1:
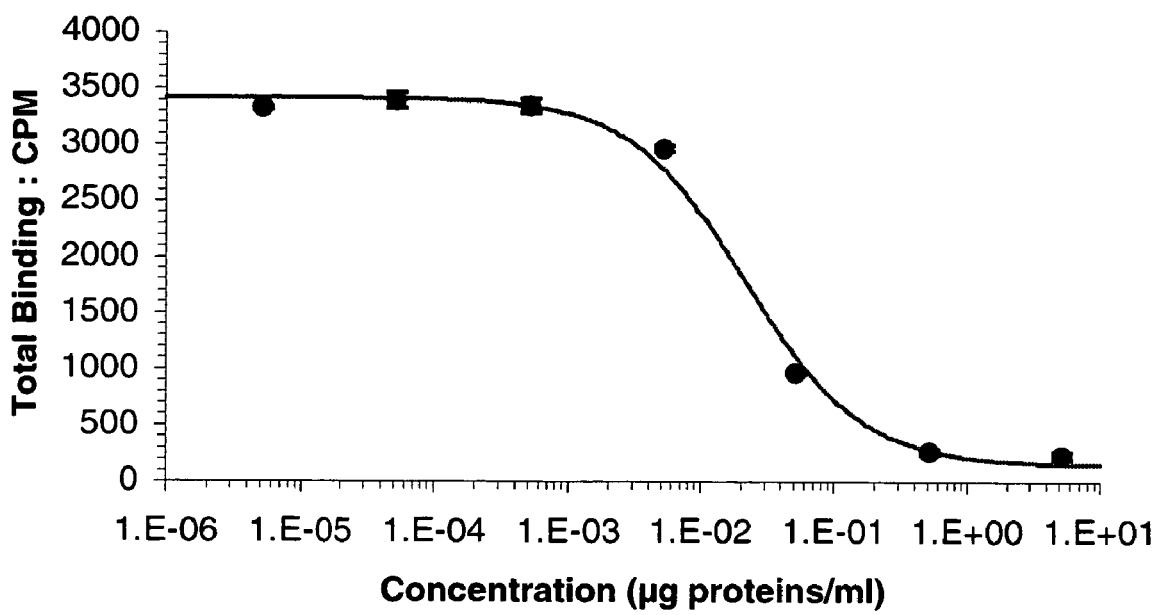
FIG. 1 is a graph representing the inhibition of binding of human GHRH on the human GHRH receptor as a function of increasing concentrations of heterocarpine.
Figure 2:
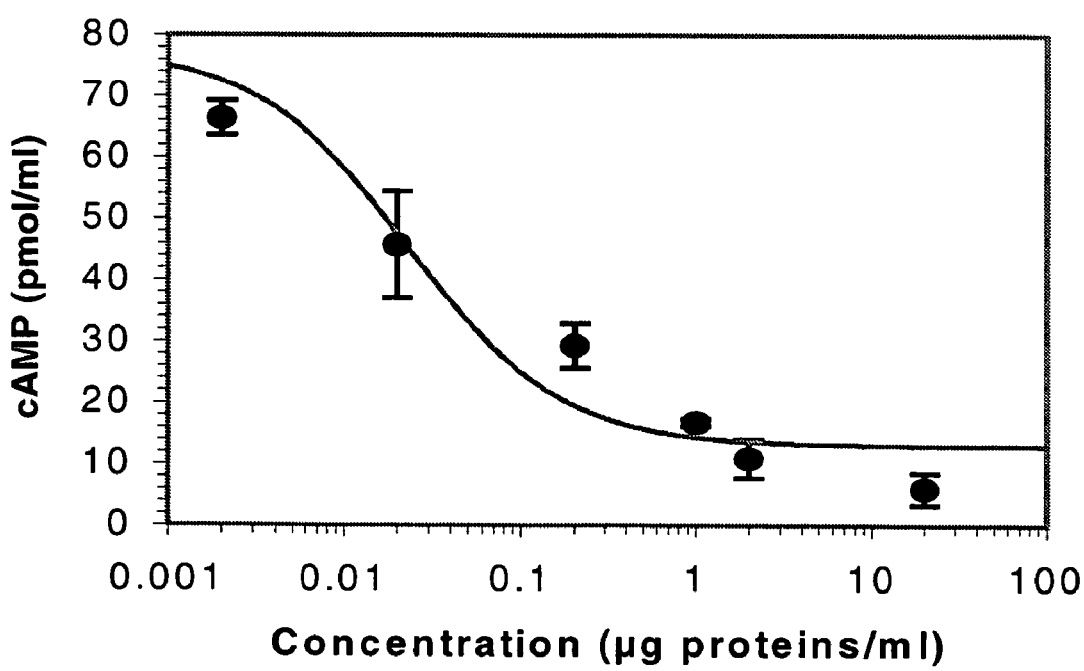
FIG. 2 is a graph representing the inhibition of the production of cyclic AMP in cells transfected in a stable manner with the human GHRH receptor in the presence of 10 nM of human GHRH as a function of increasing concentrations of heterocarpine.
Figure 3:
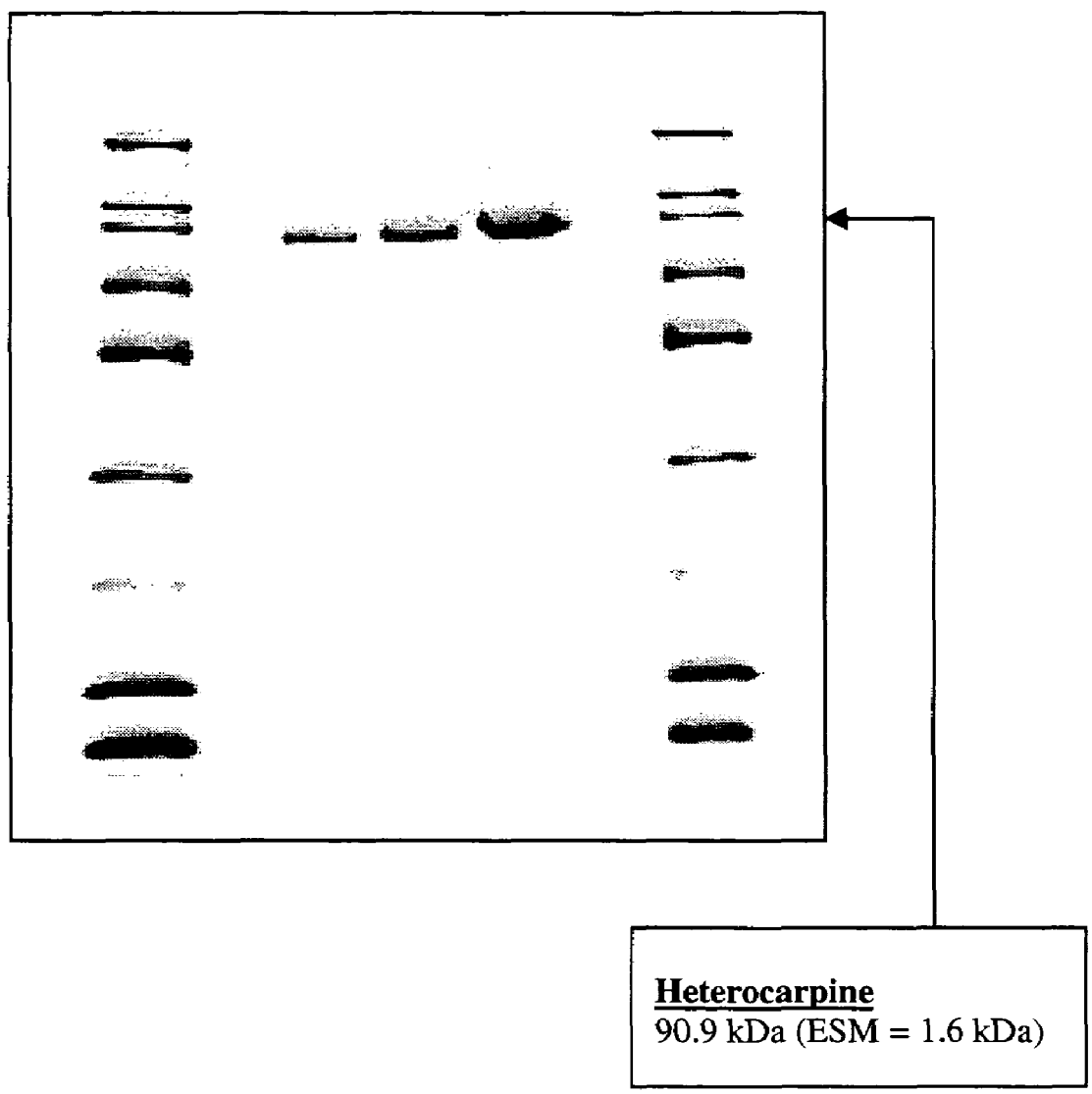
FIG. 3 is a reproduction of an SDS-PAGE protein gel plate showing the presence of heterocarpine having a molecular weight of 90.9 kDa.
Figure 4:
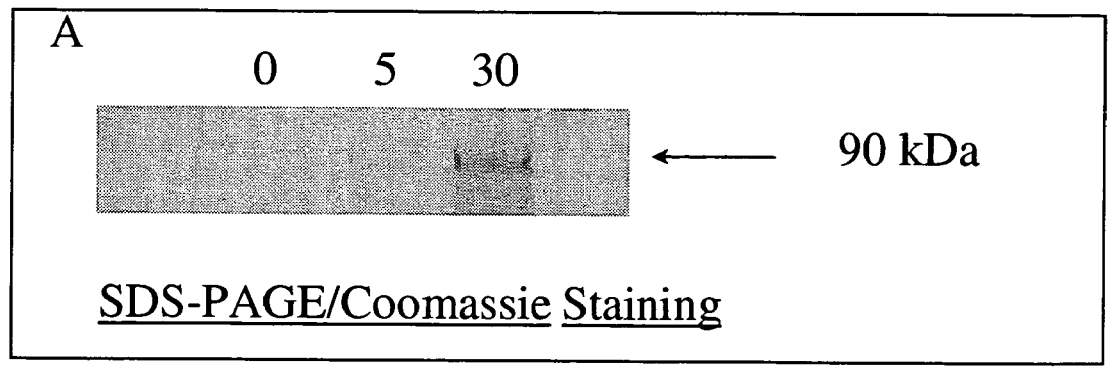
FIG. 4 is a reproduction of an SDS-PAGE protein gel plate showing that heterocarpine is a glycoprotein (Panel B).
Figure 4:
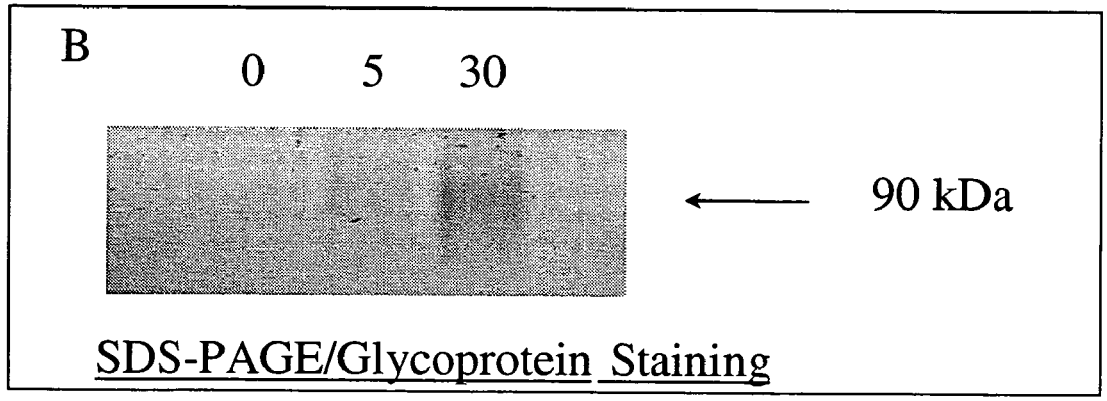
Figure 5:
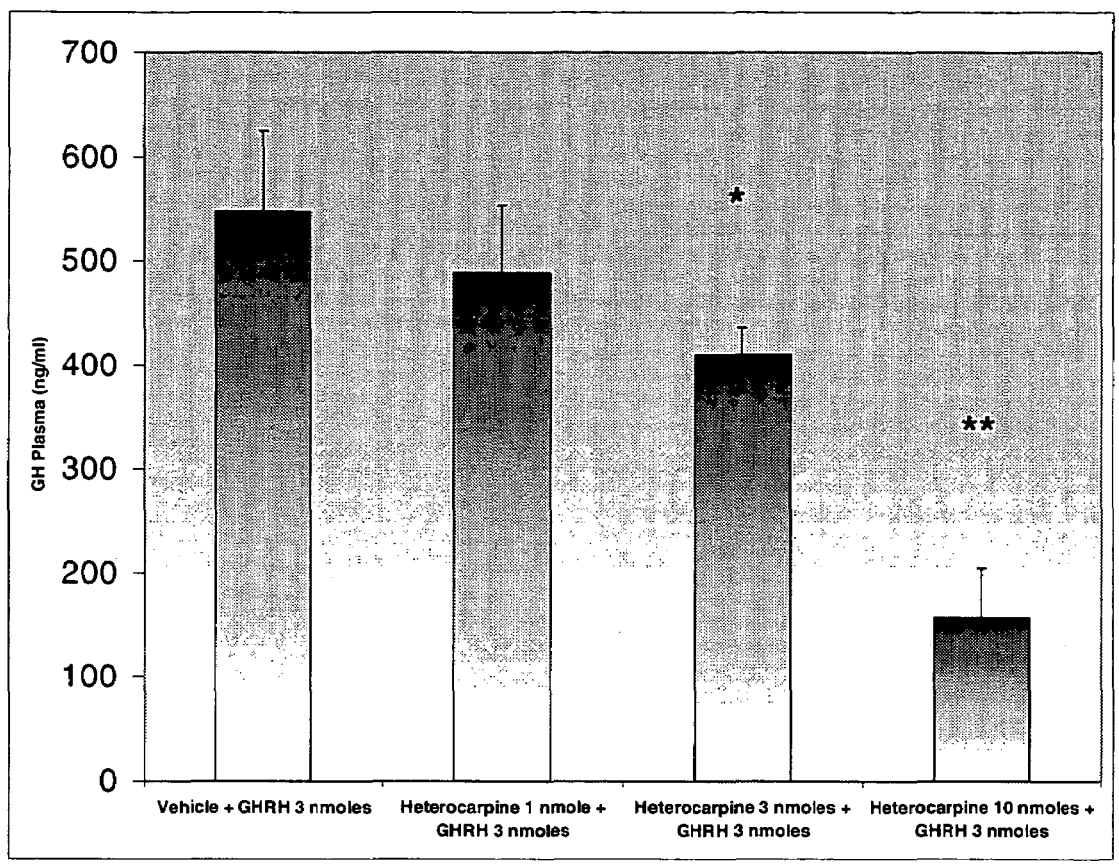
FIG. 5 is a representation in histogram form representing the inhibition of GH synthesis in rats in the presence of 10 µg of human GHRH as a function of increasing concentrations of heterocarpine.

<210> SEQ ID NO 1
<211> LENGTH: 10
<212> TYPE: PRT
<213> ORGANISM: Pilocarpus Heterophyllus

<400> SEQUENCE: 1

Lys Leu Ile Gly Ala Arg Tyr Phe Asp Lys
 1               5                  10

<210> SEQ ID NO 2
<211> LENGTH: 14
<212> TYPE: PRT
<213> ORGANISM: Pilocarpus Heterophyllus

<400> SEQUENCE: 2

```
Tyr Gly Glu Asp Ile Ile Val Gly Val Ile Asp Ser Gly Val
  1               5                  10

<210> SEQ ID NO 3
<211> LENGTH: 6
<212> TYPE: PRT
<213> ORGANISM: Pilocarpus Heterophyllus

<400> SEQUENCE: 3

Pro Glu Ser Glu Ser Tyr
  1               5
```

The invention claimed is:

1. An isolated protein obtained by extraction from the plant *Pilocarpus heterophyllus*, having a molecular mass of approximately 90.9 kDa and having a partial protein sequence consisting of SEQ.ID.NO.1, SEQ.ID.NO.2 and SEQ.ID.NO.3; said protein being in a glycosylated or non-glycosylated form.

2. A protein of claim 1 wherein it has been obtained from an extract from cells of the plant *Pilocarpus Heterophyllus* cultured in vitro.

3. An anticancer composition comprising an effective amount of the isolated protein of claim 1 sufficient to inhibit GH synthesis and an inert pharmaceutical carrier.

4. A process for the preparation of an isolated protein of claim 1 comprising extracting cells of the plant *Pilocarpus heterophyllus* with water at 0 to 50° C., filtering the aqueous extract to recover a heterocarpine-rich filtrate and recovering heterocarpine from the filtrate.

* * * * *